US007037900B2

(12) United States Patent
DiMartino et al.

(10) Patent No.: US 7,037,900 B2
(45) Date of Patent: May 2, 2006

(54) COMPOSITION AND METHOD FOR TREATING GRAFT-VERSUS-HOST DISEASE

(75) Inventors: Jorge DiMartino, San Carlos, CA (US); John Tippett Nelson, Danville, CA (US)

(73) Assignee: SuperGen, Inc., Dublin, CA (US)

( * ) Notice: Subject to any disclaimer, the term of this patent is extended or adjusted under 35 U.S.C. 154(b) by 0 days.

(21) Appl. No.: 09/976,468

(22) Filed: Oct. 12, 2001

(65) Prior Publication Data

US 2003/0073649 A1    Apr. 17, 2003

(51) Int. Cl.
*A01N 43/40* (2006.01)
*A61K 31/70* (2006.01)

(52) U.S. Cl. ............................ 514/43; 514/42; 514/45; 514/49

(58) Field of Classification Search ................... 514/42, 514/43, 45, 46, 49
See application file for complete search history.

(56) References Cited

U.S. PATENT DOCUMENTS

| 5,635,156 | A | | 6/1997 | Ildstad | 424/1.49 |
| 5,800,539 | A | * | 9/1998 | Waller | 623/11 |
| 5,876,692 | A | | 3/1999 | Ildstad | 424/1.49 |
| 5,916,910 | A | | 6/1999 | Lai | 514/423 |
| 6,174,873 | B1 | * | 1/2001 | Wrenn, Jr. | 514/45 |
| 6,258,357 | B1 | * | 7/2001 | Spanner | 424/93.71 |

OTHER PUBLICATIONS

Trotta et al. Cancer Research, 1981, vol. 41, pp. 2189-2196.*
Akpek "Graft-Versus-Host Disease (GVHD) An Evidence-Based Management Guidelines", Turk. J. Haematol. (2003), vol. 20(3), pp. 123-142.*
JF Seymour et al., Response Duration And Recovery of CD4+ Lymphocytes Following Deoxycoformaycin in Intereron- α -resistant Hairy Cell Leukemia: 7-year Follow-Up, Leukemia (1997) 11. pp. 42-47.
G. Dighiero, "Potential Immunological Action of Purine Nucleoside Analogues", Drugs 47 (Suppl. 6) 1994, pp. 57-62.
Eric H. Krout et al., "Immunosuppressive Effects of Pentostatin", Journal of Clinical Oncology, vol. 8, No. 5 (May 1990) pp. 848-855.
Joshua Epstein et al., "Prevention of Graft-Versus-Host Disease in Allogeneic Bone Marrow Transplantation by PreTreatment With 2'-Deoxycoformycin", International Society for Experimental Hematology (1986), pp. 845-849.
Paul P. Trotta et al., "Specific Immunosuppressive Effects of Constant Infusion of 2-Deoxycoformycin," Cancer Research, Jun. 1981, pp. 2189-2196.

Appelbaum, F., "Allogeneic Stem-Cell Transplantation for Hematological Malignancies", 1 ed. *Medical Management of Hematological Malignant Diseases*, ed. E. Freireich. vol. 1. 1998, New York: Marceil Dekker. 572.
Armitage, J., "Bone Marrow Transplantation", *The New England Journal of Medicine*, (1994). 330(12):827-838.
Bagasra, O. et al., "Adenosine-deaminase-associated immunodeficiency. I. Differential sensitivities of lymphocyte subpopulations exposed to 2-deoxycoformycin in vivo", *Clinical & Experimental Immunology*, (1992), 88(3):383-388.
Beatty, P. et al., "Marrow transplantation from HLA-matched unrelated donors for treatment of hematologic malignancies", *Transplantation*, (Feb. 1991), 51(2):443-447.
Bolanos-Meade, J. et al., "Pentostatin in steroid-refractory acute graft-versus-host disease", *Journal of Clinical Oncology*, (Apr. 20, 2005), 23(12):2661-2668.
Catovsky, D. "Clinical experience with 2'-deoxycoformycin", *Hematology & Cell Therapy*, (1996), 38(S2):S103-S107.
Catovsky; D. et al., "Long term results with 2'deoxycoformycin in hairy cell leukemia", *Leukemia & Lymphoma*, (1994). 14(S1):109-113.
Cummings, F.J. et al., "Phase II trial of pentostatin in refractory lymphomas and cutaneous T-cell disease", *Journal of Clinical Oncology*, (Apr. 1991), 9(4):565-571.
Epstein J. et al., "Prevention of graft-versus-host disease in allogeneic bone marrow transplantation by pretreatment with 2'-deoxycoformycin", *Experimental Hematology*, 1986. 14(9): p. 845-849.
Ferrara, J., "Cytokine Inhibitors and Graft-versus-Host Disease", *Annals New York Academy of Sciences*, (Dec. 29,1995), 770:227-236.
Foss, F.M. et al., "Phase II study of pentostatin and intermittent high-dose recombinant interferon alfa-2a in advanced mycosis fungoides/Sezary syndrome", *Journal of Clinical Oncology*, (Dec. 1987), 10(12):1907-1913.
Giblett, E.R. et al., "Adenosine-deaminase Deficiency in Two Patients With Severely Impaired Immunity", *Lancet*, (Nov. 18, 1972). 2:1067-1069.

(Continued)

*Primary Examiner*—Patrick Lewis
(74) *Attorney, Agent, or Firm*—Wilson Sonsini Goodrich & Rosati

(57) ABSTRACT

Compositions and methods are provided for prevention and clinical treatment of various forms of graft-versus-host disease (GVHD) by using inhibitors of adenosine deaminase (ADA). In particular, various formulations and dosing regimens of ADA inhibitors such as pentostatin are provided for the treatment of humans in vivo as well as for ex vivo conditioning of organ transplants in order to specifically suppress T-lymphocyte mediated immune responses while minimizing systemic toxicity of the drug.

39 Claims, No Drawings

OTHER PUBLICATIONS

Grever, M. et al., "Optimal treatment for untreated patients with hairly cell leukemia?", 1996 ASCO Abstract Form, *Journal of Clinical Oncology*, (Oct. 1995), 13(10):2677-2679.

Grever M. et al., "Randomized comparison of pentostatin versus interferon alfa-2a in previously untreated patients with hairy cell leukemia: an intergroup study", Comment in: *J Clin Oncol.*, (Oct. 13, 1995), 13(10):2677-2679.

Grever, M. et al., "Low dose doxycoformycin in lymphoid malignancy", *Journal Clinical Oncology*, (Sep. 1985), 3(9): 1196-1201.

Grever, M.R. et al., "Clinical Pharmacokinetics of 2-Deoxycoformycin in Renal Impairment", *Proceedings of ASCO*, (1993), 12(361):140.

Grever, M.R. et al., "Inhibition of K and NK Lymphocyte Cytotoxicity by an Inhibitor of Adenosine Deaminase and Deoxyadenosine", *The Journal Of Immunology*, (Dec. 1982), 129(6):365-369.

Khouri, I.F. et al., "Allogeneic blood or marrow transplantation for chronic lymphocytic leukemia: timing of transplantation and potential effect of fludarabine on acute graft-versus-host disease", *British Journal of Hematology*, (May 1997), 97(2):466-473.

Kolb, H-J et al., "Graft-versus-leukemia effect of donor lymphocyte transfusions in marrow grafted patients", *Blood*, (Sep. 1, 1995), 86(5):2041-2050.

Kraut, E.H. et al., "Immunosuppressive effects of pentostatin", *Journal of Clinical Oncology*, (1990), 8(5): 848-855.

Kraut, E.H. et al., "Low-Dose Deoxycoformycin in the Treatment of Hairy Cell Leukemia", *Blood*, (1986). 68(5): 1119-1122.

Kraut, E.H. et al., "Pentostatin in the Treatment of Advanced Hairy Cell Leukemia", *Journal of Clinical Oncology*, (1989), 7(2):168-172.

Lee, S.J., "New approaches for preventing and treating chronic graft-versus-host disease", *Blood*, (Jun. 2005), 105 (11):4200-4206.

Margolis, J. et al., ASH (1999), *Blood*, 94 # 10 Suppl 1 abstract 4878.

Margolis, J. et al., ASH (2000), *Blood* 96 #11 abstract 1723.

Martin, P.J. et al., "A retrospective analysis of therapy for acute graft-versus-host disease: initial treatment", *Blood*, (Oct. 15, 1990), 76(8):1464-1472.

Martin, P.J. et al., "A retrospective analysis of therapy for acute graft-versus-host disease: secondary treatment", *Blood*, (Apr. 15, 1991), 77(8):1821-1828.

Monfardini, S. et al., "Pentostatin (2'-deoxycoformycin, dCF) in patients with low-grade (B-T-cell) and intermediate- and high-grade (T-cell) malignant lymphomas: phase II study of the EORTC Early Clinical Trials Group", *Oncology*, 1996. 53(2):163-168.

Nash, R.A. et al., "Acute graft-versus-host disease: analysis of risk factors after allogeneic marrow transplantation and prophylaxis with cyclosporine and methotrexate", *Blood*, (Oct. 1, 1992), 80(7):1838-1845.

Or, R. et al., "Fludarabine monophosphate reduces the incidence and severity of graft-versus-host disease in a murine model of bone marrow transplantation", *Blood*, (Jul. 1, 1997), 90(1):471-476.

Przepiorka, D. et al., "Consensus Conference on Acute GVHD Grading", *Bone Marrow Transplantation*, (Jun. 1995), 15(6):825-828.

Ruers, T.J.M. et al., "Inhibition of Lymphocyte-Specific Enzymes: A Promising Approach for Selective Immunosuppression", *Transplantation Proceedings*, (Feb. 1987), 19(1): 1287-1289.

Saven, A. et al., "Newer purine analogues for the treatment of hairy-cell leukemia", *New England Journal of Medicine*, (Mar. 10, 1994). 330(10):691-697.

Seymour, J.F. et al., "Response duration and recovery of CD4+ lymphocytes following deoxycoformycin in interferon-alpha-resistant hairy cell leukemia: 7-year follow-up", *Leukemia*, (1997), 11(1):42-47.

Steis, R.G. et al., "Kinetics of recovery of CD4+ T cells in peripheral blood of deoxycoformycin-treated patients", *Journal of the National Cancer Institute*, (Nov. 20, 1991), 83(22):1678-1679.

Urba, W.J. et al., "Deoxycoformycin-Induced Immunosuppression in Patients With Hairy Cell Leukemia", *Blood*, (Jan. 1989), 73(1):38-46.

Vogelsang, G. et al., "Graft-Versus-Host Disease: New Directions for a Persistent Problem", *Blood*, (Oct. 1, 1994), 84(7):2061-2067.

Abe, Y. et al., "Eradication of virus-infected T-cells in a case of adult T-cell leukemia/lymphoma by nonmyeloblative peripheral blood stem cell transplantation with conditioning consisting of low-dose total body irradiation and pentostatin", Case Report, *International Journal of Hematology*, (Jul. 2002), 76(1):91-93.

Alcindor, T. et al., "Engraftment and immunoligic effects a novel less myeloablative allogeneic transplant conditioning regimen of continuous infusion pentostatin, photopheresis, and low dose TBI", *PROC. Blood*, (2000), 96(11):327a, abst 5160.

Bayer, R. et al., "Pentostatin based non-myeloablative conditioning regimen in patients with high-risk hematologic malignancy", *Proc of ASH*, (2000), 96(11):327, abst 5163.

Bociek, G.R. et al., Nonmyeloablative allogeneic stem cell transplantation (NST) for lymphoid maignancies using pentostatin/low-dose total body irradiation, *BB&MT*, (Feb. 2004), 10(2), Supplement 1, p. 27.

Chan, G. et al., "Decreased acute and chronic graft versus host disease with early full donor engraftment following a pentostatin-based preparative regimen for allogeneic bone marrow translpant in high-risk patients", *Proc Blood*, (2001), 98(11):383a, abst 1612.

Chan, G.W. et al., "Age is not associated with adverse outcomes following pentostatin-based preparative regimen for allogeneic bone marrow transplant", *Proc Blood*, (2001), 98(11):313b, abst 5011.

Chan, G.W. et al., "Even coagulase negative staphylococcus infections following reduced intensity transplantation are associated with increased transplant complications and poorer overall survival", *BB&MT*, (Feb. 2004), 10(2), Supplement 1, p. 11.

Chan, G.W. et al., "Extracorporeal photopheresis, pentostatin and total body irradiation reduced intensity transplantation in relapsed or refractory AML patients: evidence for early graft versus tumor effect with less GVHD", *Blood*, (Nov. 16, 2003), 102(11), abst 3265.

Chan, G.W. et al., "Grade 2-4 acute graft-versus-host disease and extensive chronic graft-versus-host disease are associated with significantly decreased survival following reduced intensity allogeneic stem cell transplanatation", *Blood*, (Nov. 16, 2004), abst 1246.

Chan, G.W. et al., "MDS patients undergoing a novel reduced intensity allogeneic bone marrow transplant achieves complete remission with less transplant toxicity and graft versus host disease", *Proc. ASH*, (2002), abst 2450.

Chan, G.W. et al., "Persistence of host dendritic cells after transplantation is associated with graft-versus-host disease", (2003), 9:170-176.

Chan, G.W. et al., "Reduced-intensity transplantation for patients with myelodysplastic syndrome achieves durable remission with less graft-versus-host disease", *Biology of Blood and Marrow Transplantation,* (2003), 9:753-759.

Chan, G.W. et al., "Targeting host antigen-presenting cells pre-transplant reduces graft versus host disease", *BB&MT,* (2002), 8(2).

Chin, K.M. et al., "Favorable outcomes in matched unrelated donor allogeneic stem cell transplantation using a pentostatin/extracorporeal photopheresis based reduced intensity conditioning regimen", *Blood,* (Nov. 16, 2003), 102(11), abst 1758.

Epstein, J. et al., "Prevention of graft-versus-host disease in allogeneic bone marrow transplantation by pretreatment with 2'-deoxycoformycin", *Exp. Hematol.,* (1986), 14:845-849.

Foss, F. et al., "Novel pentostatin/extracorporeal photopheresis based allogeneic conditioning regimen for high risk non-Hogkin's lymphoma", *Annals of Oncology,* vol. 13, Supp. 2, p. 167, Abst 597.

Foss, F. et al., "Novel pentostatin/extracorporeal photopheresis reduced intensity conditioning regimen: results in relapsed/refractory NHL", *Proc. ASH,* (2002), abst 413.

Liu, D. et al., "Graft-versus-lymphoma effect yields high percentage of durable complete remission in high risk patients following mini-transplantation with MAP (mitoxantrone, ARA-C, and pentostatin) regimen", *BB&MT,* (Feb. 2004), 10(2), Supplement 1, p. 35.

Miller, K., "Reduced intensity allogeneic transplants", *Cancer Investigation,* (Nov. 2002), vol. 21, Supp. 1, pp. 97-99.

Miller, K.B. et al., "Allotransplants: a novel reduced intensity regimen", *Cancer Investigation,* (Nov. 2000), vol. 20, Supp. 1, abst 82.

Miller, K.B. et al., "Reduced intensity conditioning regimens—a novel reduced intensity regimen for allogeneic hematopoietic stem cell transplantation associated with a reduced incidence of graft-versus-host disease", *Bone Marrow Transplantation,* (2004), 33:881-889.

Pavletic, S.Z. et al., "Immunological effects of pentostatin in a minimally myelosuppressive regimen for allogeneic stem cell transplantation", *Proc. ASH,* (2002), abst 2446.

Pavletic, S.Z. et al., "Immunomodulatory effects of pentostatin in a regimen for non-myeloablative stem cell transplantation", 3$^{rd}$ International Workshop on iwNST held on Jan. 18-21, 2002 in Captiva Island, FL, 1 page.

Pavletic, S.Z. et al., "Lymphodepleting effects and safety of pentostatin for nonmyeloablative allogeneic stem-cell transplantation", Brief Communications, *Transplantation,* (Sep. 15, 2003), 76(5):877-881.

"Pentostatin effective as preparative regimen for kidney transplant", *Expert Review of Anticancer Therapy,* (2001), 1(4):508.

Rao, R. et al., "Cytomegalovirus reactivation and relapse following allogeneic stem cell transplantation using a reduced intensity conditioning regimen", *Blood,* (Nov. 16, 2004), 104(11), abst 5104.

Roberts, T.F. et al., "A novel preparative regimen assoiciated with reduced morbidity and mortality following allogeneic bone marrow transplant", *PROC. Blood,* (2000), 96(11): 781a, abst 3378.

Roberts, T.F. et al., "Outcome of 48 patients undergoing allogeneic bone marrow transplant with a reduced intensity preparative regimen of photopheresis, continuous infusion pentostatin and reduced dose TBI", *Journal of the American Society for Blood and Marrow Transplantation,* (2002), 8(2).

Ruers, T.J. et al., "Complete suppression of skin allograft rejection in rats treated with continuous infusion of 2'-deoxycoformycin", *Transplantation,* (1985), 40(2):137-142.

Sandmaier, B.M. et al., "Conversion of low donor chimerism following nonmyeloablative conditioning for hematopoietic cell transplantation (HCT) using pentostatin and donor lymphocyte infustion (DLI)", *Blood,* (Nov. 16, 2004), 104(11), abst 186.

Schiller, G.J. et al., "Transplantation of allogeneic peripheral blood progenitor cells after non-myelosuppressive preparative conditioning—A phase I/II trial of single-agent pentostatin as an innovative preparative regimen for allogeneic transplantation for kidney cancer", *Proc of ASH,* (2001), 98(11):184a, abst 773.

Schwartz, J.E. et al., "Pensotatin and cyclosporine, a new regimen for the prevention of acute graft-versus-host disease after allogeneic peripheral blood progenitor cell transplantation", *BB&MT,* (Feb. 2004), 10(2), Supplement 1, p. 50.

Schwartz, J.E. et al., "Pentostatin and cyclosporine for prevention of acute graft-versus-host disease after allogeneic peripheral blood progeitor cell transplantation", *Blood,* (Nov. 16, 2003), 102(11), abst 5524.

Arai, S. et al., "Management of graft-versus-host disease", *Blood Reviews* (2000) 14:190-204.

De Lima, M., "GVHD Prophylaxis With Tacrolimus, Minimethotrexafe, and Pentostatin: A Phase I/II Study", Revitalization of Pentostatin: A New Approach To The Management of GVHD and Allogeneic Transplants. Satellite Symposium at the 2004 Tandem BMT meetings. Feb. 15, 2004; Orlando, Florida.

De Lima, M. et al., "Pentostatin, Tacrolimus, and "Mini"-Methotrexate for Graft-Versus-Host Disease (GVHD) Prophylaxis: A Phase I/II Controlled, Randomized Study", *Blood,* (Nov. 16, 2004), 104(11), abst 727.

Foss, F. et al., "Reduced-Intensity Conditioning for Allogeneic Transplantation", Revitalization of Pentostatin: A New Approach To The Management of GVHD and Allogeneic Transplants. Satellite Symposium at the 2004 Tandem BMT meetings. Feb. 15, 2004; Orlando, Florida.

Higman, M. et al., "Pentostatin—Pharmacology, immunology, and clinical effects in graft-versus-host disease", *Expert Opinion,* (2004) 5(12): 2605-2613.

Jacobsohn, D. et al., "Novel Pharmacotherapeutic Approaches to Prevention and Treatment of GVHD", *Drugs* 2002; 62(6): 879-889.

Jacobsohn, D. et al., "Pentostatin: Efficacy in Refractory Chronic GVHD in Children", *Blood,* (Nov. 16, 2004), 104 (11), abst 2249.

Sandmaier, B. et al., "Nonmyeloablative Hematopoietic Cell Transplantation for Patients With Hematologic Malignancies", Revitalization of Pentostatin: A New Approach To The Management of GVHD and Allogeneic Transplants. Satellite Symposium at the 2004 Tandem BMT meetings. Feb. 15, 2004; Orlando, Florida.

Goldberg, Jenna D., et al., "Pentostatin For The Treatment of Chronic Graft-Versus-Host Disease in Children," *Journal of Pediatric Hematology/Oncology* (2003, vol. 25, No. 7, pp. 584-588.

\* cited by examiner

COMPOSITION AND METHOD FOR TREATING GRAFT-VERSUS-HOST DISEASE

BACKGROUND OF THE INVENTION

1. Field of the Invention

This invention relates to compositions and methods for the treatment of graft-versus-host disease, and more specifically to the administration of inhibitors of adenosine deaminase such as pentostatin and analogs and derivatives thereof.

2. Description of Related Art

For dysfunctional and/or diseased organs of the body, besides therapeutic invention with drugs, organ transplantation is an alternative, sometimes the last resort in the treatment of the patient. Particularly for patients with leukemia, end-stage renal, cardiac, pulmonary or hepatic failure, organ transplantation is quite commonly used in the treatment. For example, allografts (organ grafts harvested from donors other than the patient him/herself or host/recipient of the graft) of various types, e.g. kidney, heart, lung, liver, bone marrow, pancreas, cornea, small intestine and skin (e.g. epidermal sheets) are currently routinely performed. Xenografts (organ grafts harvested from non-human animals), such as porcine heart valves, are also being used clinically to replace their dysfunctional human counterparts.

To ensure successful organ transplantation, it is desirable to obtain the graft from the patient's identical twin or his/her immediate family member. This is because organ transplants evoke a variety of immune responses in the host, which results in rejection of the graft and graft-versus-host disease (hereinafter, referred to as "GVHD").

The immune response is primarily triggered by T cells through recognition of alloantigens, and the major targets in transplant rejection are non-self allelic forms of class I and class II Major Histocompatibility Complex (MHC) antigens. In acute rejection, donor's antigen-presenting cells such as dendritic cells and monocytes migrate from the allograft to the regional lymph nodes, where they are recognized as foreign by the recipient's $CD4^+$ $T_H$ cells, stimulating $T_H$ cell proliferation. Following $T_H$ cells proliferation, a population of effector cells (including cytotoxic $CD8^+$ T cells and $CD4^+$ T cells) is generated, which migrates and infiltrates to the graft and mediates graft rejection (Noelle et al. (1991) FASEB 5(13):2770).

Whereas acute rejection is a T cell-dependent process, a broad array of effector mechanisms participates in graft destruction. Through the release of cytokines and cell-to-cell interactions, a diverse assembly of lymphocytes including $CD4^+$ T cells, $CD8^+$ cytotoxic T cells, antibody-forming B cells and other proinflammatory leukocytes, is recruited into the anti-allograft response. Antigen-presenting graft cells are destroyed directly by cytotoxic $CD8^+$ T cells. Activated $CD4^+$ T cells produce interleukin-2 (hereinafter, referred to as "IL-2"), which is essential to the activation of both $CD8^+$ T cells and B cells. Additionally, $CD4^+$ T cells produce other cytokines such as IFN-γ and IL-4 that also contribute to the destruction of allograft. Furthermore, interferon-γ (hereinafter, referred to as "IFN-γ") induces increased expression of class I and class II MHC molecules on graft tissue, which is more readily attacked by alloreactive effector cells. IFN-γ enhances macrophage activity and affects many inflammatory cells leading to delayed-type-hypersensitivity reaction and inflammation causing nonspecific damage to the graft. These reactions appear to be the primary cause of the early acute rejection that may occur within the first few weeks after transplant. If untreated, acute rejection progresses to a rapid and severe process that causes destruction of the transplant within a few days.

On the other hand, when a T-lymphocyte from the donor recognizes the differences based on a set of genetic markers, generally referred to as human leukocyte antigens (HLA), and it starts to attack the new body, i.e., the patient's body. Although most patients and donors are matched as closely as possible for HLA markers. Many minor markers, however, differ between donors and patients except when the patient and donor are identical twins. Before a transplant, extensive typing of the donor and recipient is performed to make sure that the donor and recipient are very close immunologically. Despite this typing there are immunological differences that cannot be detected and that the T-lymphocytes in the donor graft are capable of detecting. As a result, the donor T-lymphocytes start to attack the patient's body and cause GVHD.

There are two forms of GVHD: the acute and chronic GVHD. Acute GVHD usually occurs within the first three months following a transplant. T-cells present in the donor's bone marrow at the time of transplant attack the patient's skin, liver, stomach, and/or intestines. The earliest signs of acute GVHD are usually a skin rash that appears on the hand, feet and face. Other than blistering skin, patients with severe GVHD also develop large amounts of watery or bloody diarrhea with cramping due to the donor's T-cells' attack on the stomach and intestines. Jaundice (yellowing of the skin and eyes) is the usual indication that GVHD disease involves the liver. The more organs involved and the worse the symptoms, the worse the GVHD disease.

In the case of bone marrow transplantation, in particular, GVHD is another obstacle to survival of transplanted patients. Storb (1984) "Pathophysiology and prevention of graft-versus-host disease." In Advances in Immunobiology: Blood cell antigens and bone marrow transplantation, McCullogh and Sandier, editors, Alan, Inc., N.Y., p.337. A large proportion of GVHD-afflicted individuals dies as a result of GVHD. Weiden et al. (1980) "Graft-versus-host disease in allogeneic marrow transplantation", in Biology of Bone-Marrow Transplantation, Gale and Fox, editors, Academic Press, N.Y., p37.

To protect patients from such fatal damages, various immunosuppressive agents have been employed. Currently, allograft rejection is controlled using immunosuppressive agents such as cyclosporin A, azathioprine, corticosteroids including prednisone, and methylprednisolone, cyclophosphamide, and FK506. Cyclosporin A, the most powerful and most frequently used immunosuppressant, revolutionized the field of organ transplant surgery. Other immunosuppressive agents such as FK506, rapamycin, mycophenolic acid, 15-deoxyspergualin, mimoribine, misoprostol, OKT3 and anti-IL-2 receptor antibodies, have been used in the treatment and/or prevention of organ transplantation rejection. Briggs, Immunology letters, 29(1-2), 89–94, 1991; FASEB 3:3411, 1989. Although the development of new immunosuppressive drugs has led to substantial improvement in the survival of patients, these drugs are associated with a high incidence of side effects such as nephrotoxicity and/or hepatotoxicity.

For example, cyclosporin A has associated toxicities and side effects when used even at therapeutic doses. Although FK506 is about 10 to 100 times more potent than cyclosporin A in inhibiting activation-induced IL-2 transcription in vitro and graft rejection in vivo, it also shows side effects such as neurotoxicity and nephrotoxicity. Thus, there still exists the need for treatment and prophylaxis for GVHD with improved toxicity profiles.

SUMMARY OF THE INVENTION

Compositions and methods are provided for prevention and clinical treatment of various forms of graft-versus-host disease (GVHD) by using inhibitors of adenosine deaminase (ADA). In particular, novel formulations and dosing regimens of ADA inhibitors such as pentostatin are provided for the treatment of humans in vivo as well as for ex vivo conditioning of organ transplants in order to specifically suppress T-lymphocyte mediated immune responses while minimizing systemic toxicity of the drug.

In one aspect, a method is provided for treating a patient having graft-versus-host disease. The method comprises: administering to the patient an adenosine deaminase (ADA) inhibitor in a pharmaceutically effective amount. Examples of the adenosine deaminase inhibitor include, but are not limited to, pentostatin, fludarabine monophosphate, and cladribine. The ADA inhibitor may be administered orally or parenterally (e.g., via intravenous infusion or injection) to the patient.

The patient may have acute or chronic graft-versus-host disease, and may have also failed at least one immunosuppressive regimen such as a regimen including steroids (e.g., prednisone and methylprednisolone), cyclophosphamide, cyclosporin A, FK506, thalidomide, azathioprine, and daclizumab.

In one embodiment, the method is used to treat hematopoietic stem cell transplant (HSCT) patients manifesting grade 2 or greater acute GVHD, who have failed to respond to treatment with at least 2 mg/Kg of methylprednisolone or equivalent corticosteroid or other salvage therapy. For example, the HSCT patient may be treated with pentostatin at 0.25–1 mg/m$^2$/day as a 20 minute intravenous (IV) infusion on days 1, 2 and 3.

The method may further comprise: monitoring the improvement of the GVHD symptoms in the skin, mouth, fascia, and liver. Treatment with pentostatin may be repeated to further reduce the symptoms or to prevent recurrence of the disease.

In another embodiment, the method is used to treat steroid-refractory chronic graft vs host disease (cGVHD). For example, recipients of allogeneic HSCT developing cGVHD who have failed to respond to treatment with at least 2 mg/Kg of methylprednisolone or equivalent corticosteroid or other salvage therapy may be treated with pentostatin. For example, pentostatin may be orally administrated to the chronic GVHD patient at a dose between about 1–10 mg/m$^2$, preferably between about 2–6 mg/m$^2$, and more preferably between about 2–4 mg/m$^2$ each day for 3 consecutive days each month.

In another aspect, a method is provided for preventing or reducing the risk of developing graft-versus-host disease in a recipient of an organ or tissue transplant. The method comprises: administering to the transplant recipient an adenosine deaminase (ADA) inhibitor in a pharmaceutically effective amount within a predetermined time window before or after the transplantation. Examples of the ADA inhibitor include, but are not limited to, pentostatin, fludarabine monophosphate, and cladribine. The ADA inhibitor may be administered orally or parenterally (e.g., via intravenous infusion or injection) to the recipient of organ transplatation.

In one embodiment, pentostatin is administered orally to the transplant recipient 3 or 2 days before the transplantation. Alternatively, pentostatin may be administered to the transplant recipient by IV infusion at a dose lower than 2 mg/m$^2$, preferably at a dose lower than 1 mg/m$^2$.

In a variation of the embodiment, the transplant recipient is transplanted with hematopoietic stem cells and treated in a myeloablative conditioning regimen. The recipient may be treated with pentostatin via oral administration at about 0.5–2.0 mg/m$^2$ on days −14, −13, −12 and −3, −2, −1 with high dose cyclophosphamide and/or busulfan and/or melphalan and/or 1200–1800 cGy irradiation prior to stem cell infusion. Post transplantation the recipient may be continuously treated with pentostatin, on days +8 and +15 preferably iv at a lower dose such as 1–2 mg/m$^2$.

In another embodiment, pentostatin may be administered to a transplant recipient after the transplantation. For example, for standard (i.e., myeloablative) transplant or non-myeloablative stem cell transplant (NST) where pentostatin is not used in the conditioning regimen, pentostatin is administered to the transplant recipient at 0.5–1.5 mg/m$^2$/day on days +8, +15, +22 and +30 following stem cell infusion.

The above methods may further comprise: administering to the GVHD patient or the transplant recipient an immunosuppressive agent selected from the group consisting of prednisone, methylprednisolone, cyclophosphamide, cyclosporin A, FK506, thalidomide, azathioprine, Daclizumab, Infliximab, MEDI-205, abx-cbl and ATG.

In yet another aspect, a method is provided for ex vivo or in vitro treatment of blood derived cells, bone marrow transplants, or other organ transplants. The method comprises: treating a tissue or organ transplant with an ADA inhibitor in an effective amount such that activity of T-lymphocytes therein is substantially inhibited, preferably by at least 50% reduction in activity, more preferably by at least 80% reduction in activity, and most preferably by at least 90% reduction in activity.

Examples of the tissue or organ transplant include, but are not limited to, stem cells, bone marrow, heart, liver, kidney, lung, pancreas, small intestine, cornea, and skin. Examples of the ADA inhibitor include, but are not limited to, pentostatin, fludarabine monophosphate, and cladribine.

In one embodiment, the transplant is stored in a preservation solution containing pentostatin in an amount sufficient to inhibit activity of T-lymphocytes of the transplant. An example of commercially available preservation solutions is Plegisol (Abbott). The preservation solution may also contain conventional co-solvents, excipients, stabilizing agents and/or buffering agents.

In another embodiment, the transplant is washed with a buffer containing pentostatin prior to storage or transplantation. In this way, the risk of developing acute GVHD upon transplantation should be significantly reduced, and the host is not only protected from GVHD but also from potential side effects of pentostatin.

DETAILED DESCRIPTION OF THE INVENTION

The present invention provides methods for prevention and clinical treatment of various forms of graft-versus-host disease (GVHD) by using inhibitors of adenosine deaminase (ADA). In particular, novel formulations and dosing regimens of ADA inhibitors such as pentostatin are provided for the treatment in order to specifically suppress T-lymphocyte mediated immune responses while minimizing systemic toxicity of the drug, especially myelosuppression.

In essence, the methods operate by exploiting the effects of certain adenosine analogs such as pentostatin on ADA-dependent T-lymphocytes. It is believed that pentostatin asserts potent inhibitory effects on ADA, which ultimately leads to apoptosis of T-lymphocytes (i.e., T-cells). However, physiological functions of B-cells that are T-cell independent and hemopoietic stem cells are largely unaffected. By exploiting the preferential toxic effects of an ADA inhibitor on T-cells, patients can be treated with the drug prior to or within a time window post transplantation to prevent onset of GVHD or organ rejection. Further, patients with acute or chronic GVHD can be treated with the drug to reduce the pathological symptoms with minimal myelosuppression. In addition, the ADA inhibitor may be used for ex vivo treatment or conditioning of transplants to specifically activate T-lymphocytes from the donor without substantially affecting rate of engraftment.

The following sections describe in detail the mechanisms of actions of the ADA-inhibitors, their formulations and methods of the use for prevention and clinical treatment of GVHD, and for ex vivo conditioning of the transplants 1. Adenosine Deaminase (ADA) and its Inhibitors ADA is a 41 kD protein expressed in all tissues with highest expression in lymphocytes. ADA participates in the purine metabolism where it degrades either adenosine or 2'-deoxyadenosine producing inosine or 2'-deoxyinosine, respectively. It has been found that the activity of ADA is subject to changes depending upon the degree of activity of the cell, i.e. whether differentiation or proliferation occurs (Trotta, P. P. and Balis M. E. (1977) Cancer Research 37: 2297–2305). A genetic deficiency of ADA may cause severe combined immunodeficiency. Dighiero, G. (1996) "Adverse and beneficial immunological effects of purine nucleoside analogues," *Hematol Cell Ther,* 38:575–581.

Certain adenosine analogs have been found to have inhibitory effects on ADA. These compounds include, but are not limited to, pentostatin (2'-deoxycoformycin, also referred to as dCF, or NIPENT®); fludarabine monophosphate (FLU), a fluorinated analogue of adenine that is relatively resistant to adenosine-deaminase, and cladribine (2-chloro-2'-deoxyadenosine or 2CDA) which is also resistant to adenosine deaminase through introduction of a chlorine at the 2 carbon. These adenosine analogs that inhibits ADA activity and/or cause abnormal accumulation of deoxyadenosine and adenosine in the cell are herein collectively referred to as "ADA inhibitors".

While the exact nature of the ADA pathway intervention by these ADA inhibitors seems unclear, it may be that these compounds that are resistant to cellular deamination might mimic the ADA-deficient state. Lack of ADA seems to lead to a build up of deoxyadenosine and adenosine triphosphate in the cell, thus fatally accelerating DNA strand breaks in the cell. Under normal conditions, cells are continuously breaking and rejoining DNA. When this physiological process is accelerated by the effect of excess adenosine triphosphate, it leads to consumption of NAD for poly-ADP-ribose synthesis. This polymer is produced from nicotinamide adenosine dinucleotides (NAD) in a reaction catalyzed by the chromatin-associated poly(ADP-ribose) synthetase, leading to a depletion of the NAD content of the cell. This depletion induces a profound alteration of cellular reducing power, because of lethal ADP and ATP depletion.

The result is programmed cell death through activation of a $Ca^{2+}$-, $Mg^{2+}$-dependent endonuclease. Hence, it appears that the ADA inhibitors according to the invention can act on cells, with preferential lymphocytic activity, via an apoptotic process. The fact that supplementation of a cell medium with the NAD precursor of nicotinamide or 3-aminobenzamide, an inhibitor of poly (ADP-ribose) synthetase, prevented NAD depletion and reduces 2CDA toxicity, tends to support this hypothesis.

The ADA inhibitors listed above may affect the ADA pathway in different manners but ultimately leads accumulation of adenosine triphosphate and promotes apoptosis of cells, especially lymphocytes that have low levels of the nucleoside-cleaving enzyme 5'-nucleotidase are particularly sensitive to these antimetabolic effects. Pentostatin, for example, has been shown to be an irreversible inhibitor of ADA. By favoring the predominance of deoxycytidine kinase (DCK) over the dephosphorylating enzyme 5-nucleotidase in lymphocytes it induces a preferential accumulation of deoxyadenosine-5'-triphosphate (dATP). By comparison, FLU and 2CDA are rather resistant to the enzyme. Both drugs are initially phosphorylated by DCK and contribute to the accumulation of cellular adenosine triphosphate surrogates. As noted above, the accumulation of adenosine triphosphate, whether by the presumed pentostatin mechanism, or the FLU or 2CDA mechanism, promotes the apoptotic death of the cell.

Pentostatin has been widely used as an antimetabolite to treat various forms of leukemia in the clinic. C. Dearden, et al., "Deoxycoformycin in the treatment of mature T-cell leukemias", *Brit J. of Can.,* 64(5):903–906 (November 1991); J. Seymour et al., "Response duration and recovery of CD4+ lymphocytes following deoxycoformycin in interferon-α-resistant hairy cell leukemia: 7-year follow-up", *Leukemia,* 11, 42–47 (1997); J. Johnston et al., "Induction of Apoptosis in CD4+ Prolymphocytic Leukemia by Deoxyadenosine and 2'-Deoxycoformycin", *Leukemia Research,* 16:8, 781–788 (1992); E. Copelan et al., "Pharmacologic Marrow Purging in Murine T Cell Leukemia", *Blood,* 71(6): 1656–1661 (June 1988).

According to the present invention, it is believed that ADA inhibitors can be used to preferentially targeting T-lymphocytes, including those from the donor. By reducing T-lymphocytes presumably through apoptosis caused by the ADA inhibitor, attack of the donor T-lymphocytes on the host's organs may be prevented or significantly compromised.

2. Formulations of ADA Inhibitors

The present invention provides novel formulations and dosing regimens of ADA inhibitors for treating GVHD. By using the methodology of the present invention, GVHD may be treated in a more efficacious and convenient way and with a more favorable myelotoxicity profile. In a preferred embodiment, the ADA inhibitor is delivered orally for the treatment or prevention of GVHD. Optionally, the ADA inhibitor may be delivered mucosally or nasally for the treatment or prevention of GVHD. Alternatively, the ADA inhibitor may be delivered parenterally, in particular, intravenously. Preferably, the ADA inhibitor is delivered at a lower dose than those used in an oncological treatment.

1) ADA Inhibitors

The ADA inhibitor referred within is a composition that has an inhibitory effect on biochemical activity of adenosine deaminase (ADA). Examples of the ADA inhibitor include, but are not limited to, pentostatin, fludarabine monophosphate, and cladribine. Other ADA inhibitor may be adenosine analogs that compete with adenosine for binding to ADA such as 2'-deoxyadenosine, 3'-deoxyadenosine, and dideoxyadenosine.

Optionally, the ADA inhibitor is in the form of a therapeutically acceptable salt. This salt may be prepared in the conventional manner. Salt formers that may, for example, be used are conventional anions or salts thereof that are physiologically acceptable in the salt form. Examples thereof are: amino acids such as tyrosine or asparagine, sulfates, phosphates, carboxylic acids, tosylates, nitrates, acetates, and long chain fatty acid derivatives of these.

Should the ADA inhibitor be used in the form of a salt, the salt former may also be used in excess, i.e. in an amount greater than equimolar.

2) Oral Formulation of ADA Inhibitors

In one aspect, the ADA inhibitor is formulated for oral administration. Currently, pentostatin, for example, that is used in the clinic for treating hairy cell leukemia is formulated for intravenous (IV) administration. There are a few practical limitations associated with such a dosage form. For example, IV dosing is expensive. It requires a highly trained medical professional to administer the IV dose. The dosing involves expensive equipment and materials. Additionally, IV dosing presents increased possibilities of infection, through use of contaminated equipment or accidental contamination, for example. This is a special concern in health care settings where increased incidences of antibiotic resistant bacteria are being noted.

An oral dosage form may alleviate most, if not all, of the above-mentioned problems associated with IV or other parenteral dosage forms. However, it is well recognized in the art that deoxyadenosine analogs such as pentostatin is highly acid-labile. They are highly susceptible to acid-catalyzed glycosidic cleavage. Therefore, one of ordinary skill in the art would expect that an orally administered adenosine analog would be cleaved in the stomach, and rendered inactive. In fact, investigators studying pentostatin, have not considered oral administration of the drug worth studying because of its known acid lability. Marvin M. Chassin et al. "Enzyme Inhibition Titration Assay for 2'-deoxycoformycin and its Application to the Study of the Relationship Between Drug Concentration and Tissue Adenosine Deaminase in Dogs and Rats" Biochemical Pharmacology 28:1849–1855 (1979). Likewise, other researchers have reported on the acid lability of 2'-deoxycoformycin. L. A. al-Razzak et al. "Chemical Stability of Pentostatin (NSC-218321), a Cytotoxic and Immunosuppressant Agent", Pharm. Res. 7:452–460 (1990).

Other ADA inhibitors may be expected to have similar acid lability characteristics. A. Tarasiuk et al. "Stability of 2-chloro-2'-deoxyadenosine at Various pH and Temperature" Arch. Immunol. Ther. Exp. (Warsz) 42:13–15 (1994); T. Ono "2'-Fluoro Modified Nucleic Acids: Polymerase-directed Synthesis, Properties and Stability to Analysis by Matrix-Assisted Laser Desorption/Ionization Mass Spectrometry" Nucleic Acids Res. 25:4581–4588 (1997).

Against this mainstream of thought the inventors believe that the ADA inhibitors can be formulated for oral administration and conveniently used to treat various forms of GVHD. It is also believed that it is possible to achieve bioavailability of the ADA inhibitor using an oral dosage form and the effects of the drug on the patient in an oral dosage form should be reasonably close to those achieved using an IV dosage form.

Various oral dosage forms of the ADA inhibitor may be used in the practice of the invention. For example, the ADA inhibitor may be mixed with a pharmacologically acceptable liquid and swallowed. The ADA inhibitor also may be compounded into tablets, capsules, pills, lozenges, etc. using conventional compounding techniques.

In one embodiment, the ADA inhibitor may be administered with various agents to reduce acid concentration in the stomach. This reduces acid lability and allows for enhanced concentrations of the ADA inhibitor for enhanced gastric and/or intestinal absorption. For example, the adenosine analog may be coadministered with an H2 inhibitor such as cimetidine, an acid neutralizer such as calcium carbonate, or a proton pump inhibitor.

Furthermore, the ADA inhibitor may be (co)administered using a dosage form that reduces the effect of acid lability on their bioavailability. (Co)administration within the context of this invention may be taken to mean administration, coadministration, or both. Coadministration in the context of this invention may be defined to mean the administration of more than one therapeutic in the course of a coordinated treatment to achieve an improved clinical outcome. Such coadministration may also be coextensive, that is, occurring during overlapping periods of time.

In one variation, the ADA inhibitor such as pentostatin is formulated in a dosage form that reduces acid lability of the compound, thereby enhancing the bioavailability the compound. For example, pentostatin may be compounded with polymer matrices that are erodible chemically or biologically.

Optionally, the ADA inhibitor may be coated with an enteric coating to prevent ready decomposition in the stomach. The enteric coating may comprise hydroxypropylmethylcellulose phthalate, methacrylic acid-methacrylic acid ester copolymer, polyvinyl acetate-phthalate and cellulose acetate phthalate.

The dosage form of the ADA inhibitor may also be a solid dispersion with a water soluble or a water insoluble carrier. Examples of water soluble or water insoluble carrier include, but are not limited to, polyethylene glycol, polyvinylpyrrolidone, hydroxypropylmethylcellulose, phosphatidylcholine, polyoxyethylene hydrogenated castor oil, hydroxypropylmethylcellulose phthalate, carboxymethylethylcellulose, or hydroxypropylmethylcellulose, ethyl cellulose, or stearic acid.

Optionally, oral dosage form of the ADA inhibitor may be a complex between an ion exchange resin and the ADA inhibitor.

In another aspect, the ADA inhibitor may be formulated for a controlled release. Controlled release within the scope of this invention can be taken to mean any one of a number of extended release dosage forms.

The following terms may be considered to be substantially equivalent to controlled release, for the purposes of the present invention: continuous release, controlled release, delayed release, depot, gradual release, long-term release, programmed release, prolonged release, proportionate release, protracted release, repository, retard, slow release, spaced release, sustained release, time coat, timed release, delayed action, extended action, layered-time action, long acting, prolonged action, repeated action, slowing acting, sustained action, sustained-action medications, and extended release. Further discussions of these terms may be found in Lesczek Krowczynski "Extended-Release Dosage Forms", 1987 (CRC Press, Inc.).

The various controlled release technologies cover a very broad spectrum of drug dosage forms. Controlled release technologies include, but are not limited to physical systems and chemical systems.

Physical systems include, but not limited to, reservoir systems with rate-controlling membranes, such as microencapsulation, macroencapsulation, and membrane systems; reservoir systems without rate-controlling membranes, such as hollow fibers, ultra microporous cellulose triacetate, and porous polymeric substrates and foams; monolithic systems, including those systems physically dissolved in non-porous, polymeric, or elastomeric matrices (e.g., non-erodible, erodible, environmental agent ingression, and degradable), and materials physically dispersed in non-porous, polymeric, or elastomeric matrices (e.g., non-erodible, erodible, environmental agent ingression, and degradable); laminated structures, including reservoir layers chemically similar or dissimilar to outer control layers; and other physical methods, such as osmotic pumps, or adsorption onto ion-exchange resins.

Chemical systems include, but are not limited to, chemical erosion of polymer matrices (e.g., heterogeneous, or homogeneous erosion), or biological erosion of a polymer matrix (e.g., heterogeneous, or homogeneous). Additional discussion of categories of systems for controlled release may be found in Agis F. Kydonieus, "Controlled Release Technologies: Methods, Theory and Applications" 1980 (CRC Press, Inc.).

Controlled release drug delivery systems may also be categorized under their basic technology areas, including, but not limited to, rate-preprogrammed drug delivery systems, activation-modulated drug delivery systems, feedback-regulated drug delivery systems, and site-targeting drug delivery systems.

In rate-preprogrammed drug delivery systems, release of drug molecules from the delivery systems "preprogrammed" at specific rate profiles. This may be accomplished by system design, which controls the molecular diffusion of drug molecules in and/or across the barrier medium within or surrounding the delivery system. Fick's laws of diffusion are often followed.

In activation-modulated drug delivery systems, release of drug molecules from the delivery systems is activated by some physical, chemical or biochemical processes and/or facilitated by the energy supplied externally. The rate of drug release is then controlled by regulating the process applied, or energy input.

In feedback-regulated drug delivery systems, release of drug molecules from the delivery systems may be activated by a triggering event, such as a biochemical substance, in the body. The rate of drug release is then controlled by the concentration of triggering agent detected by a sensor in the feedback regulated mechanism.

In a site-targeting controlled-release drug delivery system, the drug delivery system targets the active molecule to a specific site or target tissue or cell. This may be accomplished, for example, by a conjugate including a site specific targeting moiety that leads the drug delivery system to the vicinity of a target tissue (or cell), a solubilizer that enables the drug delivery system to be transported to and preferentially taken up by a target tissue, and a drug moiety that is covalently bonded to the polymer backbone through a spacer and contains a cleavable group that can be cleaved only by a specific enzyme at the target tissue.

While a preferable mode of controlled release drug delivery will be oral, other modes of delivery of controlled release compositions according to this invention may be used to treat or prevent GVHD. These include mucosal delivery, nasal delivery, ocular delivery, transdermal delivery, parenteral controlled release delivery, vaginal delivery, rectal delivery and intrauterine delivery. All of these dosage forms may be manufactured using conventional techniques, together with the techniques discussed herein.

There are a number of controlled release drug formulations that are developed preferably for oral administration. These include, but are not limited to, osmotic pressure-controlled gastrointestinal delivery systems; hydrodynamic pressure-controlled gastrointestinal delivery systems; membrane permeation-controlled gastrointestinal delivery systems, which include microporous membrane permeation-controlled gastrointestinal delivery devices; gastric fluid-resistant intestine targeted controlled-release gastrointestinal delivery devices; gel diffusion-controlled gastrointestinal delivery systems; and ion-exchange-controlled gastrointestinal delivery systems, which include cationic and anionic drugs. Additional information regarding controlled release drug delivery systems may be found in Yie W. Chien "Novel Drug Delivery Systems" 1992 (Marcel Dekker, Inc.). Some of these formulations will now be discussed in more detail.

Enteric coatings may be applied to tablets to prevent the release of drugs in the stomach either to reduce the risk of unpleasant side effects or to maintain the stability of the drug which might otherwise be subject to degradation due to expose to the gastric environment. Most polymers that are used for this purpose are polyacids that function by virtue of the fact that their solubility in aqueous medium is pH-dependent, and they require conditions with a pH higher than normally encountered in the stomach.

Enteric coatings may be used to coat a solid or liquid dosage form of adenosine analogs according to the invention. Enteric coatings promote the inventive adenosine analogs remaining physically incorporated in the dosage form for a specified period when exposed to gastric juice. Yet the enteric coatings are designed to disintegrate in intestinal fluid for ready absorption. Delay of the adenosine analogs absorption is dependent on the rate of transfer through the gastrointestinal tract, and so the rate of gastric emptying is an important factor. Some investigators have reported that a multiple-unit type dosage form, such as granules, may be superior to a single-unit type. Therefore, in a preferable embodiment, the ADA inhibitor according to the invention may be contained in an enterically coated multiple-unit dosage form. In a more preferable embodiment, the dosage form of the ADA inhibitor according to the invention is prepared by spray-coating granules of an adenosine analog-enteric coating agent solid dispersion on an inert core material. These granules can result in prolonged absorption of the drug with good bioavailability.

Typical enteric coating agents include, but are not limited to, hydroxypropylmethylcellulose phthalate, methacrylic acid-methacrylic acid ester copolymer, polyvinyl acetate-phthalate and cellulose acetate phthalate. Akihiko Hasegawa "Application of solid dispersions of Nifedipine with enteric coating agent to prepare a sustained-release dosage form" Chem. Pharm. Bull. 33: 1615–1619 (1985). Various enteric coating materials may be selected on the basis of testing to achieve an enteric coated dosage form designed ab initio to have a preferable combination of dissolution time, coating thicknesses and diametral crushing strength. S. C. Porter et al. "The Properties of Enteric Tablet Coatings Made From Polyvinyl Acetate-phthalate and Cellulose acetate Phthalate", J. Pharm. Pharmacol. 22:42p (1970).

On occasion, the performance of an enteric coating may hinge on its permeability. S. C. Porter et al., "The Permeability of Enteric Coatings and the Dissolution Rates of Coated Tablets", J. Pharm. Pharmacol. 34: 5–8 (1981). With such oral drug delivery systems, the drug release process may be initiated by diffusion of aqueous fluids across the enteric coating. Investigations have suggested osmotic driven/rupturing affects as important release mechanisms from enteric coated dosage forms. Roland Bodmeier et al. "Mechanical Properties of Dry and Wet Cellulosic and Acrylic Films Prepared from Aqueous Colloidal Polymer Dispersions used in the Coating of Solid Dosage Forms" Pharmaceutical Research, 11: 882–888 (1994).

Another type of useful oral controlled release structure is a solid dispersion. A solid dispersion may be defined as a dispersion of one or more active ingredients in an inert carrier or matrix in the solid state prepared by the melting (fusion), solvent, or melting-solvent method. Akihiko Hasegawa "Super Saturation Mechanism of Drugs from Solid Dispersions with Enteric Coating Agents", Chem. Pharm. Bull. 36: 4941–4950 (1998). The solid dispersions may be also called solid-state dispersions. The term "coprecipitates" may also be used to refer to those preparations obtained by the solvent methods.

Solid dispersions may be used to improve the solubilities and/or dissolution rates of the ADA inhibitor according to the invention that may be poorly water-soluble. Hiroshi Yuasa, et al. "Application of the Solid Dispersion Method to the Controlled Release Medicine. III. Control of the Release Rate of Slightly Water-Soluble Medicine From Solid Dispersion Granules" Chem. Pharm. Bull. 41:397–399 (1993). The solid dispersion method was originally used to enhance the dissolution rate of slightly water-soluble medicines by dispersing the medicines into water-soluble carriers such as polyethylene glycol or polyvinylpyrrolidone, Hiroshi Yuasa, et al. "Application of the Solid Dispersion Method to the Controlled Release of Medicine. IV. Precise Control of the Release Rate of a Water-Soluble Medicine by Using the Solid Dispersion Method Applying the Difference in the Molecular Weight of a Polymer" Chem. Pharm. Bull. 41:933–936 (1993).

The selection of the carrier may have an influence on the dissolution characteristics of the dispersed drug because the dissolution rate of a component from a surface may be affected by other components in a multiple component mixture. For example, a water-soluble carrier may result in a fast release of the drug from the matrix, or a poorly soluble or insoluble carrier may lead to a slower release of the drug from the matrix. The solubility of poorly water soluble adenosine analogs according to the invention may also be increased owing to some interaction with the carriers.

Examples of carriers useful in solid dispersions according to the invention include, but are not limited to, water-soluble polymers such as polyethylene glycol, polyvinylpyrrolidone, or hydroxypropylmethylcellulose. Akihiko Hasegawa, "Application of Solid Dispersions of Nifedipine with Enteric Coating Agent to Prepare a Sustained-release Dosage Form" Chem. Pharm. Bull. 33: 1615–1619 (1985).

Alternate carriers include phosphatidylcholine. Makiko Fuji, et al. "The Properties of Solid Dispersions of Indomethacin, Ketoprofen and Flurbiprofen in Phosphatidylcholine" Chem. Pharm. Bull. 36:2186–2192 (1988). Phosphatidylcholine is an amphoteric but water-insoluble lipid, which may improve the solubility of otherwise insoluble adenosine analogs in an amorphous state in phosphatidylcholine solid dispersions. See Makiko Fuji, et al., "Dissolution of Bioavailability of Phenytoin in Solid Dispersion with Phosphatidylcholine" Chem. Pharm. Bull 36:4908–4913 (1988).

Other carriers include polyoxyethylene hydrogenated castor oil. Katsuhiko Yano, et al. "In-Vitro Stability and In-Vivo Absorption Studies of Colloidal Particles Formed From a Solid Dispersion System" Chem. Pharm. Bull 44:2309–2313 (1996). Poorly water-soluble adenosine analogs according to the invention may be included in a solid dispersion system with an enteric polymer such as hydroxypropylmethylcellulose phthalate and carboxymethylethylcellulose, and a non-enteric polymer, hydroxypropylmethylcellulose. See Toshiya Kai, et al., "Oral Absorption Improvement of Poorly Soluble Drug Using Soluble Dispersion Technique", Chem. Pharm. Bull. 44:568–571 (1996). Another solid dispersion dosage form includes incorporation of the ADA inhibitor with ethyl cellulose and stearic acid in different ratios. Kousuke Nakano, et al. "Oral Sustained-Release Cisplatin Preparations for Rats and Mice" J. Pharm. Pharmacol. 49:485–490 (1997).

There are various methods commonly known for preparing solid dispersions. These include, but are not limited to the melting method, the solvent method and the melting-solvent method.

In the melting method, the physical mixture of a drug in a water-soluble carrier is heated directly until it melts. The melted mixture is then cooled and solidified rapidly while rigorously stirred. The final solid mass is crushed, pulverized and sieved. Using this method a super saturation of a solute or drug in a system can often be obtained by quenching the melt rapidly from a high temperature. Under such conditions, the solute molecule may be arrested in solvent matrix by the instantaneous solidification process. A disadvantage is that many substances, either drugs or carriers, may decompose or evaporate during the fusion process at high temperatures. However, this evaporation problem may be avoided if the physical mixture is heated in a sealed container. Melting under a vacuum or blanket of an inert gas such as nitrogen may be employed to prevent oxidation of the drug or carrier.

The solvent method has been used in the preparation of solid solutions or mixed crystals of organic or inorganic compounds. Solvent method dispersions may be prepared by dissolving a physical mixture of two solid components in a common solvent, followed by evaporation of the solvent. The main advantage of the solvent method is that thermal decomposition of drugs or carriers may be prevented because of the low temperature required for the evaporation of organic solvents. However, some disadvantages associated with this method are the higher cost of preparation, the difficulty in completely removing liquid solvent, the possible adverse effect of its supposedly negligible amount of the solvent on the chemical stability of the drug.

Another method of producing solid dispersions is the melting-solvent method. It is possible to prepare solid dispersions by first dissolving a drug in a suitable liquid solvent and then incorporating the solution directly into a melt of polyethylene glycol, obtainable below 70 degrees, without removing the liquid solvent. The selected solvent or dissolved adenosine analogs may be selected such that the solution is not miscible with the melt of polyethylene glycol. The polymorphic form of the adenosine analogs may then be precipitated in the melt. Such a unique method possesses the advantages of both the melting and solvent methods. Win Loung Chiou, et al. "Pharmaceutical Applications of Solid Dispersion Systems" J. Pharm. Sci. 60:1281–1301 (1971).

Another controlled release dosage form is a complex between an ion exchange resin and the ADA inhibitor according to the invention. Ion exchange resin-drug complexes have been used to formulate sustained-release products of acidic and basic drugs. In one preferable embodiment, a polymeric film coating is provided to the ion exchange resin-drug complex particles, making drug release from these particles diffusion controlled. See Y. Raghunathan et al. "Sustained-released drug delivery system I: Coded ion-exchange resin systems for phenylpropanolamine and other drugs" J. Pharm. Sciences 70: 379–384 (1981).

Injectable micro spheres are another controlled release dosage form. Injectable micro spheres may be prepared by non-aqueous phase separation techniques, and spray-drying techniques. Micro spheres may be prepared using polylactic acid or copoly(lactic/glycolic acid). Shigeyuki Takada "Utilization of an Amorphous Form of a Water-Soluble GPIIb/

IIIa Antagonist for Controlled Release From Biodegradable Micro spheres" Pharm. Res. 14:1146–1150 (1997), and ethyl cellulose, Yoshiyuki Koida "Studies on Dissolution Mechanism of Drugs from Ethyl Cellulose Microcapsules" Chem. Pharm. Bull. 35:1538–1545 (1987).

Other controlled release technologies that may be used in the practice of this invention are quite varied. They include SODAS, INDAS, IPDAS, MODAS, EFVAS, PRODAS, and DUREDAS. SODAS are multi particulate dosage forms utilizing controlled release beads. INDAS are a family of drug delivery technologies designed to increase the solubility of poorly soluble drugs. IPDAS are multi particulate tablet formation utilizing a combination of high density controlled release beads and an immediate release granulate. MODAS are controlled release single unit dosage forms. Each tablet consists of an inner core surrounded by a semipermeable multiparous membrane that controls the rate of drug release. EFVAS is an effervescent drug absorption system. PRODAS is a family of multi particulate formulations utilizing combinations of immediate release and controlled release mini-tablets. DUREDAS is a bilayer tablet formulation providing dual release rates within the one dosage form. Although these dosage forms are known to one of skill, certain of these dosage forms will now be discussed in more detail.

INDAS was developed specifically to improve the solubility and absorption characteristics of poorly water soluble drugs. Solubility and, in particular, dissolution within the fluids of the gastrointestinal tract is a key factor in determining the overall oral bioavailability of poorly water soluble drug. By enhancing solubility, one can increase the overall bioavailability of a drug with resulting reductions in dosage. INDAS takes the form of a high energy matrix tablet. In a preferred embodiment of the invention production involves including adenosine analogs in an amorphous form together with a combination of energy, excipients, and unique processing procedures.

Once included in the desirable physical form, the resultant high energy complex may be stabilized by an absorption process that utilizes a novel polymer cross-linked technology to prevent recrystallization. The combination of the change in the physical state of the ADA inhibitor according to the invention coupled with the solubilizing characteristics of the excipients employed enhances the solubility of the ADA inhibitor according to the invention. The resulting absorbed amorphous drug complex granulate may be formulated with a gel-forming erodable tablet system to promote substantially smooth and continuous absorption.

IPDAS is a multi-particulate tablet technology that may enhance the gastrointestinal tolerability of potential irritant and ulcerogenic drugs. Intestinal protection is facilitated by the multi-particulate nature of the IPDAS formulation which promotes dispersion of an irritant ADA inhibitor according to the invention throughout the gastrointestinal tract. Controlled release characteristics of the individual beads may avoid high concentration of drug being both released locally and absorbed systemically. The combination of both approaches serves to minimize the potential harm of the ADA inhibitor according to the invention with resultant benefits to patients.

IPDAS is composed of numerous high density controlled release beads. Each bead may be manufactured by a two step process that involves the initial production of a micromatrix with embedded adenosine analogs according to the invention and the subsequent coating of this micromatrix with polymer solutions that form a rate limiting semipermeable membrane in vivo. Once an IPDAS tablet is ingested, it may disintegrate and liberate the beads in the stomach. These beads may subsequently pass into the duodenum and along the gastrointestinal tract, preferably in a controlled and gradual manner, independent of the feeding state. The release of the ADA inhibitor occurs by diffusion process through the micromatrix and subsequently through the pores in the rate controlling semipermeable membrane. The release rate from the IPDAS tablet may be customized to deliver a drug-specific absorption profile associated with optimized clinical benefit. Should a fast onset of activity be necessary, immediate release granulate may be included in the tablet. The tablet may be broken prior to administration, without substantially compromising drug release, if a reduced dose is required for individual titration.

MODAS is a drug delivery system that may be used to control the absorption of a water soluble ADA inhibitor according to the invention. Physically MODAS is a non-disintegrating table formulation that manipulates drug release by a process of rate limiting diffusion by a semipermeable membrane formed in vivo. The diffusion process essentially dictates the rate of presentation of drug to the gastrointestinal fluids, such that the uptake into the body is controlled. Because of the minimal use of excipients, MODAS can readily accommodate small dosage size forms. Each MODAS tablet begins as a core containing active drug plus excipients. This core is coated with a solution of insoluble polymers and soluble excipients. Once the tablet is ingested, the fluid of the gastrointestinal tract may dissolve the soluble excipients in the outer coating leaving substantially the insoluble polymer. What results is a network of tiny, narrow channels connecting fluid from the gastrointestinal tract to the inner drug core of water soluble drug. This fluid passes through these channels, into the core, dissolving the drug, and the resultant solution of drug may diffuse out in a controlled manner. This may permit both controlled dissolution and absorption. An advantage of this system is that the drug releasing pores of the tablet are distributed over substantially the entire surface of the tablet. This facilitates uniform drug absorption and reduces aggressive unidirectional drug delivery. MODAS represents a very flexible dosage form in that both the inner core and the outer semipermeable membrane may be altered to suit the individual delivery requirements of a drug. In particular, the addition of excipients to the inner core may help to produce a micro-environment within the tablet that facilitates more predictable release and absorption rates. The addition of an immediate release outer coating may allow for development of combination products.

Additionally, PRODAS may be used to deliver the ADA inhibitor according to the invention. PRODAS is a multi particulate drug delivery technology based on the production of controlled release mini tablets in the size range of 1.5 to 4 mm in diameter. The PRODAS technology is a hybrid of multi particulate and hydrophilic matrix tablet approaches, and may incorporate, in one dosage form, the benefits of both these drug delivery systems.

In its most basic form, PRODAS involves the direct compression of an immediate release granulate to produce individual mini tablets that contain adenosine analogs according to the invention. These mini tablets are subsequently incorporated into hard gels and capsules that represent the final dosage form. A more beneficial use of this technology is in the production of controlled release formulations. In this case, the incorporation of various polymer combinations within the granulate may delay the release rate of drugs from each of the individual mini tablets. These mini tablets may subsequently be coated with controlled release polymer solutions to provide additional delayed release properties. The additional coating may be necessary in the case of highly water soluble drugs or drugs that are perhaps gastro-irritants where release can be delayed until the formulation reaches more distal regions of the gastrointestinal tract. One value of PRODAS technology lies in the inherent flexibility to formulation whereby combinations of mini tablets, each with different release rates, are incorporated into one dosage form. As well as potentially permitting controlled absorption over a specific period, this also may permit targeted delivery of drug to specific sites of absorption throughout the gastrointestinal tract. Combination products also may be possible using mini tablets formulated with different active ingredients.

DUREDAS is a bilayer tableting technology that may be used in the practice of the invention. DUREDAS was developed to provide for two different release rates, or dual release of a drug from one dosage form. The term bilayer refers to two separate direct compression events that take place during the tableting process. In a preferable embodiment, an immediate release granulate is first compressed, being followed by the addition of a controlled release element which is then compressed onto this initial tablet. This may give rise to the characteristic bilayer seen in the final dosage form.

The controlled release properties may be provided by a combination of hydrophilic polymers. In certain cases, a rapid release of the ADA inhibitor according to the invention may be desirable in order to facilitate a fast onset of therapeutic affect. Hence one layer of the tablet may be formulated as an immediate release granulate. By contrast, the second layer of the tablet may release the drug in a controlled manner, preferably through the use of hydrophilic polymers. This controlled release may result from a combination of diffusion and erosion through the hydrophilic polymer matrix.

A further extension of DUREDAS technology is the production of controlled release combination dosage forms. In this instance, two different ADA inhibitors according to the invention may be incorporated into the bilayer tablet and the release of drug from each layer controlled to maximize therapeutic affect of the combination.

One preferable example of coadministration is the combination of deoxyadenosines with pentostatin. This combination may operate synergistically, to obtain a differential effect over either of the therapeutic agents administered separately. It has been reported that pentostatin enhances the clinical anti-HIV activity of related adenosine analogs presumably due to prevention of degradation of the adenosine analogs by adenosine deaminase. G. S. Ahluwalia, et al., "Enhancement by 2'-deoxycoformycin of the 5"-Phosphorylation and Anti-Human immunodeficiency virus activity of 2'3'-dideoxyadenosine and 2'-beta-fluor-2', 3'-dideoxyadenosine", *Molec. Pharmacol.* 46:1002–1008 (1994).

Furthermore, the ADA inhibitor may be administered or coadministered with conventional pharmaceutical excipients and additives. These include, but are not limited to, gelatin, natural sugars such as raw sugar or lactose, lecithin, pectin, starches (for example corn starch or amylose), dextran, polyvinyl pyrrolidone, polyvinyl acetate, gum arabic, alginic acid, tylose, talcum, lycopodium, silica gel (for example colloidal), cellulose, cellulose derivatives (for example cellulose ethers in which the cellulose hydroxy groups are partially etherified with lower saturated aliphatic alcohols and/or lower saturated, aliphatic oxyalcohols, for example methyl oxypropyl cellulose, methyl cellulose, hydroxypropyl methyl cellulose, hydroxypropyl methyl cellulose phthalate), fatty acids as well as magnesium, calcium or aluminum salts of fatty acids with 12 to 22 carbon atoms, in particular saturated (for example stearates), emulsifiers, oils and fats, in particular vegetable (for example, peanut oil, castor oil, olive oil, sesame oil, cottonseed oil, corn oil, wheat germ oil, sunflower seed oil, cod liver oil, in each case also optionally hydrated); glycerol esters and polyglycerol esters of saturated fatty acids $C_{12}H_{24}O_2$ to $C_{18}H_{36}O_2$ and their mixtures, it being possible for the glycerol hydroxy groups to be totally or also only partly esterified (for example mono-, di- and triglycerides); pharmaceutically acceptable mono- or multivalent alcohols and polyglycols such as polyethylene glycol and derivatives thereof, esters of aliphatic saturated or unsaturated fatty acids (2 to 22 carbon atoms, in particular 10–18 carbon atoms) with monovalent aliphatic alcohols (1 to 20 carbon atoms) or multivalent alcohols such as glycols, glycerol, diethylene glycol, pentaerythritol, sorbitol, mannitol and the like, which may optionally also be etherified, esters of citric acid with primary alcohols, acetic acid, urea, benzyl benzoate, dioxolanes, glyceroformals, tetrahydrofurfuryl alcohol, polyglycol ethers with $C_1$-$C_{12}$-alcohols, dimethylacetamide, lactamides, lactates, ethylcarbonates, silicones (in particular medium-viscous polydimethyl siloxanes), calcium carbonate, sodium carbonate, calcium phosphate, sodium phosphate, magnesium carbonate and the like.

Other auxiliary substances that may be used are those which cause disintegration (so-called disintegrants), such as: cross-linked polyvinyl pyrrolidone, sodium carboxymethyl starch, sodium carboxymethyl cellulose or microcrystalline cellulose. Conventional coating substances may also be used to produce the oral dosage form. Those that may for example be considered are: polymerizates as well as copolymerizates of acrylic acid and/or methacrylic acid and/or their esters; copolymerizates of acrylic and methacrylic acid esters with a lower ammonium group content (for example EudragitR RS), copolymerizates of acrylic and methacrylic acid esters and trimethyl ammonium methacrylate (for example EudragitR RL); polyvinyl acetate; fats, oils, waxes, fatty alcohols; hydroxypropyl methyl cellulose phthalate or acetate succinate; cellulose acetate phthalate, starch acetate phthalate as well as polyvinyl acetate phthalate, carboxy methyl cellulose; methyl cellulose phthalate, methyl cellulose succinate, -phthalate succinate as well as methyl cellulose phthalic acid half ester; zein; ethyl cellulose as well as ethyl cellulose succinate; shellac, gluten; ethylcarboxyethyl cellulose; ethacrylate-maleic acid anhydride copolymer; maleic acid anhydride-vinyl methyl ether copolymer; styrol-maleic acid copolymerizate; 2-ethyl-hexyl-acrylate maleic acid anhydride; crotonic acid-vinyl acetate copolymer; glutaminic acid/glutamic acid ester copolymer; carboxymethylethylcellulose glycerol monooctanoate; cellulose acetate succinate; polyarginine.

Plasticizing agents that may be considered as coating substances are: citric and tartaric acid esters (acetyl-triethyl citrate, acetyl tributyl-, tributyl-, triethyl-citrate); glycerol and glycerol esters (glycerol diacetate, -triacetate, acetylated monoglycerides, castor oil); phthalic acid esters (dibutyl-, diamyl-, diethyl-, dimethyl-, dipropylphthalate), di-(2-methoxy- or 2-ethoxyethyl)-phthalate, ethylphthalyl glycolate, butylphthalylethyl glycolate and butylglycolate; alcohols (propylene glycol, polyethylene glycol of various chain lengths), adipates (diethyladipate, di-(2-methoxy- or 2-ethoxyethyl)-adipate; benzophenone; diethyl- and diburylsebacate, dibutylsuccinate, dibutyltartrate; diethylene glycol dipropionate; ethyleneglycol diacetate, -dibutyrate, -dipropionate; tributyl phosphate, tributyrin; polyethylene glycol sorbitan monooleate (polysorbates such as Polysorbar 50); sorbitan monooleate.

As mentioned above, the ADA inhibitor may be orally administered or coadministered in a liquid dosage form. For the preparation of solutions or suspensions it is, for example, possible to use water, particularly sterile water, or physiologically acceptable organic solvents, such as alcohols (ethanol, propanol, isopropanol, 1,2-propylene glycol, polyglycols and their derivatives, fatty alcohols, partial esters of glycerol), oils (for example peanut oil, olive oil, sesame oil, almond oil, sunflower oil, soya bean oil, castor oil, bovine hoof oil), paraffins, dimethyl sulphoxide, triglycerides and the like.

In the case of drinkable solutions the following substances may be used as stabilizers or solubilizers: lower aliphatic mono- and multivalent alcohols with 2–4 carbon atoms, such as ethanol, n-propanol, glycerol, polyethylene glycols with molecular weights between 200–600 (for example 1 to 40% aqueous solution), diethylene glycol monoethyl ether, 1,2-propylene glycol, organic amides, for example amides of aliphatic $C_1$-$C_6$-carboxylic acids with ammonia or primary, secondary or tertiary $C_1$-$C_4$-amines or $C_1$-$C_4$-hydroxy amines such as urea, urethane, acetamide, N-methyl acetamide, N,N-diethyl acetamide, N,N-dimethyl acetamide, lower aliphatic amines and diamines with 2–6 carbon atoms, such as ethylene diamine, hydroxyethyl theophylline, tromethamine (for example as 0.1 to 20% aqueous solution), aliphatic amino acids.

In preparing the inventive compositions, it is possible to use known and conventional solubilizers or emulsifiers. Solubilizers and emulsifiers that may for example be used are: polyvinyl pyrrolidone, sorbitan fatty acid esters such as sorbitan trioleate, phosphatides such as lecithin, acacia, tragacanth, polyoxyethylated sorbitan monooleate and other ethoxylated fatty acid esters of sorbitan, polyoxyethylated fats, polyoxyethylated oleotriglycerides, linolizated oleotriglycerides, polyethylene oxide condensation products of fatty alcohols, alkylphenols or fatty acids or also 1-methyl-3-(2-hydroxyethyl)imidazolidone-(2). In this context, polyoxyethylated means that the substances in question contain polyoxyethylene chains, the degree of polymerization of which generally lies between 2 and 40 and in particular between 10 and 20.

Polyoxyethylated substances of this kind may for example be obtained by reaction of hydroxyl group-containing compounds (for example mono- or diglycerides or unsaturated compounds such as those containing oleic acid radicals) with ethylene oxide (for example 40 Mol ethylene oxide per 1 Mol glyceride).

Examples of oleotriglycerides are olive oil, peanut oil, castor oil, sesame oil, cottonseed oil, corn oil. See also Dr. H. P. Fiedler "Lexikon der Hillsstoffe für Pharmazie, Kostnetik und angrenzende Gebiete" 1971, pages 191–195.

It is also possible to add preservatives, stabilizers, buffer substances, flavor correcting agents, sweeteners, colorants, antioxidants and complex formers and the like. Complex formers which may be for example be considered are: chelate formers such as ethylene diamine retrascetic acid, nitrilotriacetic acid, diethylene triamine pentacetic acid and their salts.

It may optionally be necessary to stabilize the ADA inhibitor with physiologically acceptable bases or buffers to a pH range of approximately 6 to 9. Preference may be given to as neutral or weakly basic a pH value as possible (up to pH 8).

In some dosage forms, it may be useful to include antioxidants or preservatives. Antioxidants that may for example be used are sodium sulphite, sodium hydrogen sulphite, sodium metabisulphite, ascorbic acid, ascorbylpalmitate, -myristate, -stearate, gallic acid, gallic acid alkyl ester, butylhydroxyamisol, nordihydroguaiaretic acid, tocopherols as well as synergists (substances which bind heavy metals through complex formation, for example lecithin, ascorbic acid, phosphoric acid ethylene diamine tetracetic acid, citrates, tartrates). Addition of synergists substantially increases the antioxygenic effect of the antioxidants.

Preservatives that may for example be considered are sorbic acid, p-hydroxybenzoic acid esters (for example lower alkyl esters), benzoic acid, sodium benzoate, trichloroisobutyl alcohol, phenol, cresol, benzethonium chloride, chlorhexidine and formalin derivatives.

The various oral dosage forms can be prepared according to conventional procedures. For example, tablets can be prepared according to common tableting procedures. Capsules can be prepared according to conventional encapsulating procedures. Liquid dosage forms may be supplied as a made-up vial, or may be supplied in a lyophilized state for dilution just prior to administration. Controlled release dosage forms may be prepared according to the particular dosage form being used, as is discussed briefly above.

3) Parenteral Formulation

Alternatively, the ADA inhibitor such as pentostatin may be formulated for parenteral administration such as intravenous infusion. In a preferred embodiment, pentostatin is parenterally administered to the patient at a lower dose than the standard dose used for treating hair cell leukemia (4 mg/m$^2$). Thus, pentostatin may be supplied as a sterile, apyrogenic, lyopholized powder in single dose vials at about 1–5 mg/vial and more preferably at 2–4 mg/vial. The vials may also contain excipients such as mannitol. Pentostatin contained in the single dose vial can be reconstituted by using sterile water, saline or other infusion fluid prior to infusion. The pH of the final infusion fluid containing low dose pentostatin is preferably maintained between 7.0 and 8.5 by addition of sodium hydroxide or hydrochloric acid.

3. Method of Use and Dosing Regimen

The ADA inhibitor may be used to treat patients with various forms of GVHD including acute and chronic GVHD that is either naive or refractory to conventional immunosuppressive agents such as steroids and cyclosporin A. The ADA inhibitor may also be used as prophylaxis to prevent onset of GVHD by pretreating the transplant recipient prior to the transplantation and/or treating the recipient within a certain time window post transplantation.

1) Treatment of GVHD

In one embodiment, a method is provided for treating a patient suffering from GVHD. The method comprises administering to the GVHD patient a composition including an ADA inhibitor.

Dosage amounts and frequency will vary according to the particular ADA inhibitor, the dosage form, and individual patient characteristics. Generally speaking, determining the dosage amount and frequency for a particular ADA inhibitor (e.g., pentostatin), dosage form, and individual patient characteristic can be accomplished using conventional dosing studies, coupled with appropriate diagnostics. In preferable embodiments, the dosage frequency ranges from daily to monthly doses, more preferably biweekly doses. In other preferable embodiments, the dosage amount ranges from about 0.02 mg/m$^2$ to about 20 mg/m$^2$, more preferably about 0.05 mg/m$^2$ to about 5 mg/m$^2$, and most preferably 0.1 mg/m$^2$ to about 1 mg/m$^2$.

A dosage amount below 1 mg/m² is considered to be much lower than the standard dose (4 mg/m² once every 2 weeks) used for the treatment of hairy cell leukemia. According to the present invention, lowering the dosage amount of pentostatin should minimize myelosuppression associated with high dose of this antimetabolic drug and yet can still specifically suppress the GVHD-causing T-lymphocyte mediated immune response.

In a particular embodiment, an ADA inhibitor such as pentostatin is used to treat patients that have acute Graft vs Host Disease (aGVHD) but failed at least one immunosuppressive regimen such as a regimen including steroids such as prednisone and methylprednisolone, cyclophosphamide, cyclosporin A, FK506, thalidomide, azathioprine, and daclizumab. For example, hematopoietic stem cell transplant (HSCT) patients manifesting grade 2 or greater aGVHD, who have failed to respond to treatment with at least 2 mg/Kg of methylprednisolone or equivalent corticosteroid or other salvage therapy, can be treated with pentostatin.

In a preferred embodiment, the HSCT patient with steroid-refractory aGVHD is treated with pentostatin according to the following plan. The patient is treated with 0.25–1 mg/m²/day as a 20 minute intravenous (IV) infusion on days 1, 2 and 3. The patient's response to the treatment is monitored by following for improvement in the skin, mouth, fascia, and liver. The same dose may be repeated after 14 days if there was response to the first 3 days of treatment that was incomplete or that recurred after a full or partial response.

Pentostatin may also be administered orally to achieve similar plasma levels as those via IV route of administration. However, for aGVHD patients with severely damaged gastrointestinal (GI) tract IV infusion may be the preferred route of administration.

In another embodiment, an ADA inhibitor such as pentostatin is used to treat steroid-refractory chronic Graft vs Host Disease (cGVHD). For example, recipients of allogeneic HSCT developing cGVHD who have failed to respond to treatment with at least 2 mg/Kg of methylprednisolone or equivalent corticosteroid or other salvage therapy, can be treated with pentostatin via IV or oral administration.

In a variation of this embodiment, pentostatin is orally administrated to the cGVHD patient at a dose between about 1–10 mg/m², preferably between about 2–6 mg/m², and more preferably between about 2–4 mg/m² each day for 3 consecutive days each month. For an average adult, a dose of 4 mg/m² would be approximately 6–8 mg/day (one and a half or two 4 mg tablets or capsules).

2) GVHD Prophylaxis

An ADA inhibitor such as pentostatin can also be used as a prophylaxis to prevent onset of GVHD or to reduce the effects of GVHD.

Pentostatin may be administered as a GVHD prophylaxis parenterally or orally to a transplant recipient within a predetermined time window before or after the transplantation.

In one embodiment, pentostatin may be administered orally to the recipient on days −3 or −2 (i.e., 3 or 2 days before the transplantation) as part of a non-myeloablative conditioning regimen, then followed by transplantation such as hematopoietic stem cell infusion. Alternatively, pentostatin may be administered to the recipient by IV infusion at a dose lower than 2 mg/m², preferably at a dose lower than 1 mg/m².

In myeloablative conditioning regimen, the transplant recipient may be treated with pentostatin p.o. (i.e., via oral administration) at 0.5–2.0 mg/m² on days −14, −13, −12 and −3, −2, −1 with high dose cyclophosphamide and/or busulfan and/or melphalan and/or 1200–1800 cGy irradiation prior to stem cell infusion. Post transplantation the recipient may be continuously treated with pentostatin, on days +8 and +15 preferably iv at a lower dose such as 1–2 mg/m² since patients receiving myeloablative conditioning might not be able to tolerate an oral dosage form on days +8 and +15 due to severe mucositis.

In another embodiment, pentostatin may be administered as a GVHD prophylaxis to a transplant recipient after the transplantation. For example, for standard (i.e., myeloablative) transplant or non-myeloablative stem cell transplant (NST) where pentostatin is not used in the conditioning regimen, pentostatin is administered to the transplant recipient at 0.5–1.5 mg/m²/day on days +8, +15, +22 and +30 following stem cell infusion.

4. Combination Therapy for GVHD

Besides use in a single-agent treatment or prevention of GVHD, the ADA inhibitor such as pentostatin can also be used in a combination therapy for acute or chronic GVHD. The combination therapy may have synergistic therapeutic effects on the patients and thus requires lower amount of pentostatin and the other agent used in conjunction to achieve satisfactory therapeutic efficacy. As a result, potential side effects associated with high dose of drugs, such as myelosuppression, are reduced and the patient's quality of life is improved.

Various other therapeutic agents may be combined with pentostatin for the treatment or prevention of GVHD. The other therapeutic agents include, but are not limited to, immunosuppressive agents such as steroids (e.g., prednisone and methylprednisolone), cyclophosphamide, cyclosporin A, FK506, thalidomide, azathioprine, monoclonal antibodies (e.g., Daclizumab (anti-interleukin (IL)-2), Infliximab (anti-tumor necrosis factor), MEDI-205 (anti-CD2), abx-cbl (anti-CD147)), and polyclonal antibodies (e.g., ATG (anti-thymocyte globulin)).

For example, pentostatin may be combined with a steroid such as methylprednisolone to treat aGVHD. However, such a combination may be too broadly immunosuppressive to render the patient more susceptible to opportunistic infection.

For the treatment of acute GVHD, pentostatin may preferably be combined with monoclonal antibodies which specifically target T-cells such as Infliximab, Daclizumab, MEDI-205, or abx-cbl. The monoclonal antibody may be administered at the FDA-approved dosage and by its standard route of administration (e.g., IV), followed by oral or parenteral administration of pentostatin as described in detail in Section 3 above.

For the treatment of chronic GVHD, pentostatin may be combined with thalidomide. Pentostatin may also be used in conjunction with other immunosuppressive agents as prophylaxis for GVHD post transplantation. For example, the recipient of bone marrow transplant may be treated with pentostatin in conjunction with a standard post infusion regimen including mini-methotrexate at 5 mg/m² (as opposed to the conventional dose at 10–15 mg/m²), cyclosporine A (5–6 mg/Kg/d IV or 10–18 mg/Kg/d orally) and FK506 (0.05–0.1 mg/Kg/d IV or 0.15–0.3 mg/Kg/d orally).

In addition, pentostatin may be used in conjunction with other types of therapy as prophylaxis for GVHD prior to transplantation. For example, the recipient of bone marrow transplant may be pretreated with pentostatin in conjunction with TBI (radiation), phototherapy, melphalan, cyclophosphamide or ATG to prevent the onset of GVHD.

5. Ex Vivo Treatment of Transplants Using ADA Inhibitors

In yet another aspect, the invention relates to a method of ex vivo or in vitro treatment of blood derived cells, bone marrow transplants, or other organ transplants. The method comprises treating the blood derived cells, bone marrow transplants, or other organ transplants with an ADA inhibitor (e.g., pentostatin) in an effective amount such that activities of T-lymphocytes therein are substantially inhibited, preferably by at least 50% reduction in activity, more preferably by at least 80% reduction in activity, and most preferably by at least 90% reduction in activity.

The invention is practiced in an in vitro or ex vivo environment. All of the discussion above regarding clinical treatment or prevention of GVHD that is relevant to an in vitro or ex vivo environment applies to this practice. In a particular embodiment, practice of an in vitro or ex vivo embodiment of the invention might be useful in the practice of immune system transplants, such as bone marrow transplants or peripheral stem cell procurement. In such procedures, the ADA inhibitor might be used, as generally described above, to treat the transplant material to inactivate T-lymphocytes therein so that the T-lymphocyte mediated immune response is suppressed upon transplantation.

For example, the ADA inhibitor may be added to a preservation solution for an organ transplant in an amount sufficient to inhibit activity of T-lymphocytes of the organ. Such a preservation solution may be suitable for preservation of different kind of organs such as heart, kidney and liver as well as tissue therefrom. An example of commercially available preservation solutions is Plegisol (Abbott), and other preservation solutions named in respect of its origins include the UW-solution (University of Wisconsin), the Stanford solution and the Modified Collins solution (J. Heart Transplant (1988) Vol. 7(6):456–4467). The preservation solution may also contain conventional co-solvents, excipients, stabilizing agents and/or buffering agents.

The dosage form of the ADA inhibitor may be a liquid solution ready for use or intended for dilution with a preservation solution. Alternatively, the dosage form may be lyophilized or power filled prior to reconstitution with a preservation solution. The lyophilized substance may contain, if suitable, conventional excipients.

The preservation solution or buffer containing an ADA inhibitor (e.g., pentostatin) may also be used to wash or rinse an organ transplant prior to transplantation or storage. For example, a preservation solution containing pentostatin may be used to flush perfuse an isolated heart which is then stored at 4° C. in the preservation solution.

In another embodiment, practice of the invention might be used to condition organ transplants prior to transplantation. Prior to transplantation pentostatin may be added to the washing buffer to rid the transplant of active T-lymphocytes. In this way, the risk of developing acute GVHD upon transplantation should be significantly reduced, and the host is not only protected from GVHD but also from potential side effects of pentostatin.

The concentration of the ADA inhibitor in the preservation solution or wash buffer may vary according to the type of transplant. For example, pentostatin at 1 µM may be used to treat an isolated heart prior to transplantation.

Other applications in vitro or ex vivo using an ADA inhibitor will occur to one of skill in the art and are therefore contemplated as being within the scope of the invention.

The invention claimed is:

1. A method for reducing the risk of developing graft-versus-host disease in a human patient who is a recipient of an organ or tissue transplant, composing:
   treating the patient with myeloablative conditioning regimen; and
   administering to the transplant recipient pentostatin in a pharmaceutically effective amount within a predetermined time window before the transplantation.

2. The method claim 1, wherein the transplant recipient is transplanted with bone marrow.

3. The method of claim 1, wherein the transplant recipient is transplanted with hematopoietic stem cells.

4. The method of claim 1, wherein pentostatin is administered orally to the transplant recipient.

5. The method of claim 1, wherein pentostatin is administered parenterally to the transplant recipient.

6. The method of claim 1, wherein pentostatin is administered to the transplant recipient by intravenous infusion at a dose of about 1–10 mg/m$^2$.

7. The method of claim 1, wherein pentostatin is administered to the transplant recipient by intravenous infusion at a dose of about 2–6 mg/m$^2$.

8. The method of claim 1, wherein pentostatin is administered to the transplant recipient by intravenous infusion at a dose of about 2 mg/m$^2$.

9. The method of claim 1, wherein pentostatin is administered to the transplant recipient by intravenous infusion at a dose of about 1 mg/m$^2$.

10. The method of claim 1, further comprising: administering to the transplant recipient an immunosuppressive agent selected from the group consisting of prednisone, methylprednisolone, cyclophosphamide, cyclosporin A, FK506, thalidomide, azathioprine, Daclizumab, Infliximab, MEDI-205, abx-cbl and ATG.

11. The method of claim 1, wherein pentostatin is administered to the patient 2 or 3 days before the transplantation.

12. A method for preventing or reducing the risk of developing graft-versus-host disease in a patient who is a recipient of an organ or tissue transplant, comprising:
    administering to the transplant recipient pentostatin in a pharmaceutically effective amount of about 1–10 mg/m2 within a predetermined time window after the transplantation.

13. The method claim 12, wherein the transplant recipient is transplanted with bone marrow, stem cells, heart, liver, kidney, lung, pancreas, small intestine, cornea, or skin.

14. The method of claim 12, wherein the transplant recipient is transplanted with hematopoietic stem cells.

15. The method of claim 12, wherein the transplant patient is treated in a myeloablative or non-myeloablative conditioning regimen.

16. The method of claim 12, wherein pentostatin is administered orally to the transplant recipient.

17. The method of claim 12, wherein pentostatin is administered parenterally to the transplant recipient.

18. The method of claim 12, wherein pentostatin is administered to the transplant recipient by intravenous infusion at a dose of about 1–10 mg/m$^2$.

19. The method of claim 12, wherein pentostatin is administered to the transplant recipient by intravenous infusion at a dose of about 2–6 mg/m$^2$.

20. The method of claim 12, wherein pentostatin is administered to the transplant recipient by intravenous infusion at a dose of about 2 mg/m$^2$.

21. The method of claim 12, wherein pentostatin is administered to the transplant recipient by intravenous infusion at a dose of about 1 mg/m$^2$.

22. The method of claim 12, further comprising: administering to the transplant recipient an immunosuppressive agent selected from the group consisting of prednisone, methylprednisolone, cyclophosphamide, cyclosporin A, FK506, thalidomide, azathioprine, Daclizumab, Infliximab, MEDI-205, abx-cbl and ATG.

23. The method of claim 1, wherein pentostatin is administered to the patient 2 or 3 days before the transplantation.

24. The method of claim 12, wherein pentostatin is administered to the transplant recipient at about 1.5 mg/m$^2$/day on day +8 following the transplantation.

25. The method of claim 25, wherein the transplant is hematopoietic stem cells or bone marrow.

26. The method of claim 12, wherein the transplant is hematopoietic stem cells or bone marrow.

27. The method of claim 27, wherein the transplant is hematopoietic stem cells or bone marrow.

28. The method of claim 12, wherein pentostatin is administered to the transplant recipient at about 1.5 mg/m$^2$/day on days +8, +15, and +22 following the transplantation.

29. The method of claim 29, wherein the transplant is hematopoietic stem cells or bone marrow.

30. The method of claim 12, wherein pentostatin is administered to the transplant recipient at about 1.5 mg/m$^2$/day on days +8, +15, +22 and +30 following the transplantation.

31. The method of claim 31, wherein the transplant is hematopoietic stem cells or bone marrow.

32. The method of claim 12, wherein the transplant recipient is transplanted with hematopoietic stem cells and treated in a myeloablative conditioning regimen.

33. The method of claim 12, wherein pentostatin is administered intravenously to the transplant recipient at 1–2 mg/m$^2$/day on days +8, following the transplantation.

34. The method of claim 12, wherein pentostatin is administered intravenously to the transplant recipient at 1–2 mg/m$^2$/day on day +15 following the transplantation.

35. The method of claim 12, wherein pentostatin is administered intravenously to the transplant recipient at 1–2 mg/m$^2$/day on days +8 and +15 following the transplantation.

36. The method of claim 12, wherein pentostatin is administered intravenously to the transplant recipient at 1–2 mg/m$^2$/day on days +8 and +15 following the transplantation.

37. The method of claim 37, wherein the transplant is myeloablative transplant.

38. The method of claim 37, wherein the transplant is non-myeloablative transplant.

39. The method of claim 12, wherein pentostatin is administered intravenously to the transplant recipient at 1.5 mg/m$^2$/day on days +8, +15, +22, and +30 following the transplantation.

* * * * *